United States Patent [19]
Chen et al.

[11] Patent Number: 5,736,159
[45] Date of Patent: Apr. 7, 1998

[54] CONTROLLED RELEASE FORMULATION FOR WATER INSOLUBLE DRUGS IN WHICH A PASSAGEWAY IS FORMED IN SITU

[75] Inventors: Chih-Ming Chen, Cooper City; Der-Yang Lee, Plantation; Jianbo Xie, Davie, all of Fla.

[73] Assignee: Andrx Pharmaceuticals, Inc., Fort Lauderdale, Fla.

[21] Appl. No.: 430,356

[22] Filed: Apr. 28, 1995

[51] Int. Cl.$^6$ ............................................. A61K 9/36
[52] U.S. Cl. ...................... 424/480; 424/474; 424/472; 424/473
[58] Field of Search .......................... 424/474, 480, 424/472, 473

[56] References Cited

U.S. PATENT DOCUMENTS

| | | |
|---|---|---|
| 3,065,143 | 11/1962 | Christenson et al. |
| 3,845,770 | 11/1974 | Theeuwes et al. |
| 4,016,880 | 4/1977 | Theeues et al. |
| 4,285,987 | 8/1981 | Ayer et al. |
| 4,369,172 | 1/1983 | Schor. |
| 4,389,393 | 6/1983 | Schor. |
| 4,704,285 | 11/1987 | Alderman. |
| 4,783,337 | 11/1988 | Wong et al. |
| 4,789,549 | 12/1988 | Khan et al. .................. 424/480 |
| 4,801,461 | 1/1989 | Hamel. |
| 5,178,866 | 1/1993 | Wright et al. .................. 424/473 |
| 5,458,887 | 10/1995 | Chen et al. .................. 424/480 |
| 5,464,633 | 11/1995 | Conte et al. .................. 424/480 |
| 5,558,879 | 9/1996 | Chen et al. .................. 424/480 |

OTHER PUBLICATIONS

Shin Etsu Bulletin, Jan. 1993.
Dow Technical Information Bulletin, Feb., 1991.

*Primary Examiner*—Amy Hulina
*Attorney, Agent, or Firm*—Hedman, Gibson & Costigan, P.C.

[57] ABSTRACT

A controlled release pharmaceutical tablet is disclosed which is based on:
(a) a compressed core which contains:
  (i) a medicament;
  (ii) at least 23% to 55% by weight, based on the total weight of the core, of a water soluble osmotic agent;
  (iii) a water soluble pharmaceutically acceptable polymeric binder;
  (iv) a water-swellable pharmaceutically acceptable polymer;
  (v) a conventional pharmaceutical excipient; and
(b) a membrane coating around said core tablet which consists essentially of:
  (i) a modified water insoluble pharmaceutically acceptable polymer; and
  (ii) a pharmaceutically acceptable water soluble polymer.

6 Claims, 7 Drawing Sheets

CONTROLLED RELEASE FORMULATION FOR WATER INSOLUBLE DRUGS IN WHICH A PASSAGEWAY IS FORMED IN SITU

BACKGROUND OF THE INVENTION

The present invention relates to controlled release unit dose formulations of pharmaceuticals. In the prior art many techniques have been used to provide controlled and extended release pharmaceutical dosage forms in order to maintain therapeutic serum levels of medicaments and to minimize the effects of missed doses of drugs caused by a lack of patient compliance.

In the prior art extended release tablets containing osmotic tablets have been described and manufactured which have had an osmotically active drug core surrounded by a semipermeable membrane. The core is divided into two layers one of which contains the active drug and the other contains a push layer of pharmacologically inactive ingredients which are osmotically active in the presence of gastrointestinal fluids. An outer water impermeable coating covers the tablet which is provided with an aperture that is formed by laser drilled orifice to allow gastrointestinal fluids to reach the osmotic push layer to activate the tablet and to begin to push out the active medicament. A product of this type is disclosed in U.S. Pat. No. 4,783,337 and is sold commercially as Procardia XL®.

The osmotic dosage forms that are disclosed in U.S. Pat. No. 4,783,337 are described as having a passageway which includes an aperture, orifice, hole, porous element, hollow fiber, capillary tube, microporous insert, pore, microporous overlay or bore which extends through the semipermeable lamina, the microporous lamina, or through the laminated wall. The patent also states that the passageway may be formed by mechanical drilling, laser drilling, eroding an erodible element, extracting, dissolving, bursting or leaching a passageway-former from the wall of the osmotic dosage form (col. 14, line 35 et seq.) which are implicitly preformed in the tablet during the manufacturing process. The only exemplified technique of forming a passageway in U.S. Pat. No. 4,783,337 is the use of a laser to drill a hole in the outer layer of the tablet.

U.S. Pat. No. 4,285,987 described an osmotic tablet which had a laser drilled aperture into the core of the tablet. The laser drilled hole was plugged with leachable sorbitol which was leached out in the presence of gastrointestinal fluid.

The present invention is concerned with providing an osmotic tablet that avoids the need to have a separate "push" layer in the core which contains no medicament and which avoids the need to have a pre-formed passageway or a leachable plug in the tablet to allow the gastrointestinal fluid to reach the osmotic core.

SUMMARY OF THE INVENTION

The present invention is directed to a controlled release pharmaceutical tablet which comprises:
(a) a compressed core which consists essentially of:
  (i) a medicament;
  (ii) at least 23% to 55% by weight, based on the total weight of the core, of a water soluble osmotic agent;
  (iii) a water soluble pharmaceutically acceptable polymeric binder;
  (iv) a water-swellable pharmaceutically acceptable polymer;
  (v) conventional pharmaceutical excipients; and (b) a membrane coating around said core tablet which consists essentially of:
  (i) a modified water insoluble pharmaceutically acceptable polymer; and
  (ii) a pharmaceutically acceptable water soluble polymer.

It is an object of the invention to provide a a controlled release pharmaceutical tablet which has an osmotic core covered with a external polymeric membrane that provides therapeutic blood levels with once a day administration.

It is also an object of the present invention to provide a controlled release pharmaceutical tablet that has an osmotic and no pre-formed aperture in the external polymeric membrane.

It is also an object of this invention to provide a controlled release pharmaceutical tablet having a single component osmotic core wherein the core component may be made using ordinary tablet compression techniques.

These and other objects of the invention will become apparent from the appended specification.

DETAILED DESCRIPTION OF THE INVENTION

The controlled release osmotic tablet formulation of the invention provides performance which is equivalent to much more complicated prior art controlled release dosage formulations which require a complex segmented osmotic core and a pre-formed aperture in the external membrane which is applied around the osmotic core.

The core of the controlled release tablet of the present invention is made by initially forming granules by combining a medicament and a water soluble osmotic agent with conventional excipients and a water soluble polymeric binder. Thereafter, the granules are blended with a water swellable polymer and suitable excipients to form a composition which may be compressed into tablets. A tabletting machine is used to compress the granule mixture into a core tablet which is subsequently coated with a water insoluble polymeric membrane to form the controlled release tablet of the invention.

Although the inventor does not wish to be bound by any theory by which the present invention operates, it is believed that the use of the plasticizer or channeling agent in combination with the water insoluble polymer to form the external membrane around the core of the tablet, results in a membrane which will allow water to be imbibed into the core of the tablet even in the absence of a pre-formed aperture. As water is taken up into the core of the tablet, the water swellable polymer expands as the water soluble osmotic agent dissolves and increases the osmotic pressure inside the tablet. This causes a very slight expansion of the partially hydrated core which is controlled by the use of a relatively small amount of the water swellable polymer.

Figure 1:
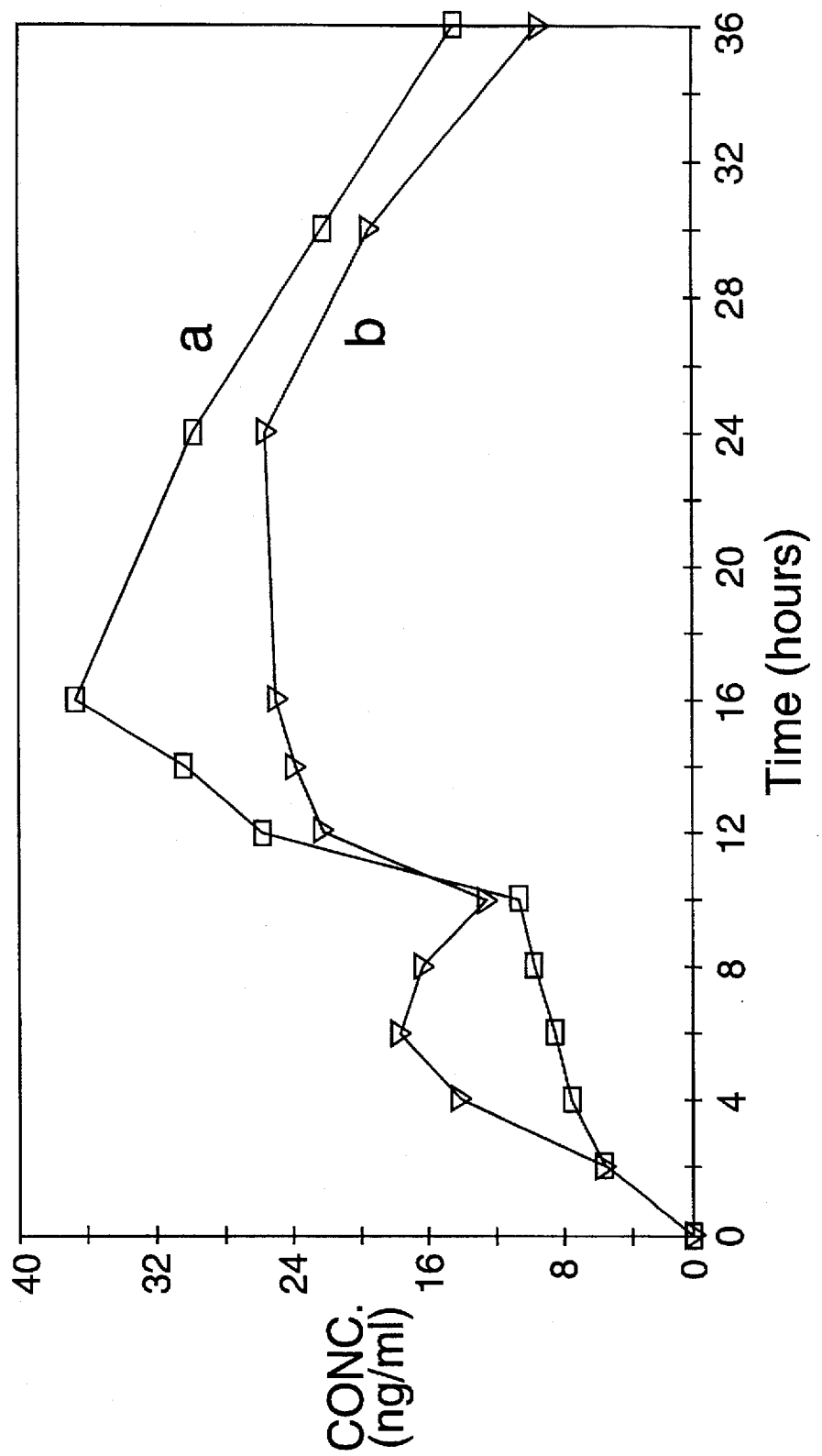
FIG. 1 is a graph which compares the mean plasma concentration of Procardia XL® (b) and a nifedipine tablet (a) prepared according to Example 1 of the present invention in a crossover study involving 6 fasting human volunteers.
Figure 2:
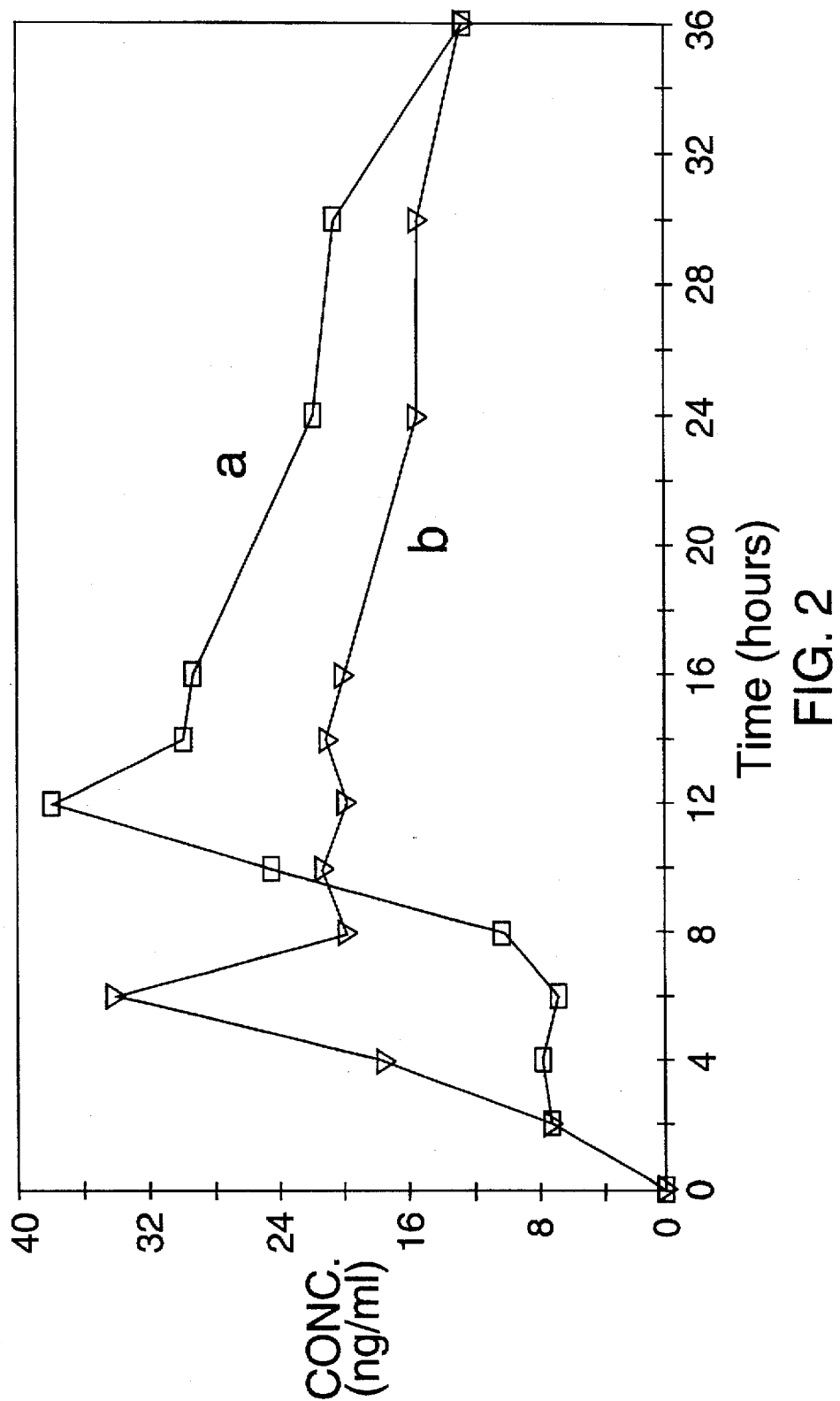
FIG. 2 is a graph which compares the mean plasma concentration of Procardia XL® (b) and a nifedipine tablet (a) prepared according to Example 1 of the present invention in a crossover study involving 6 fed human volunteers.
Figure 3:
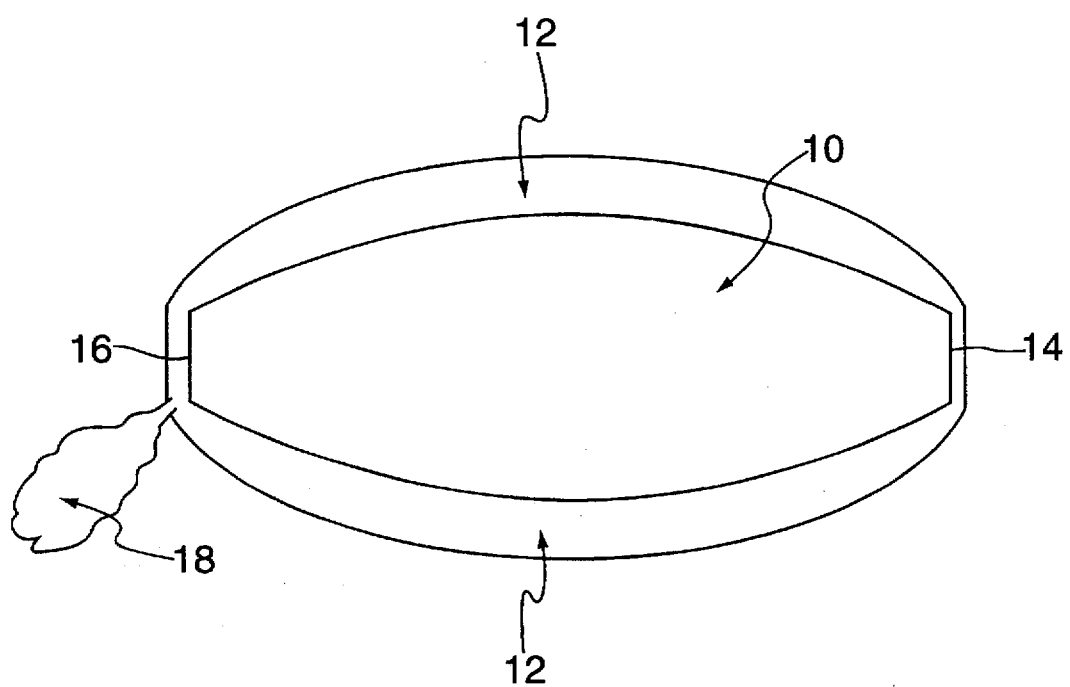
FIG. 3 is a cross-section of a tablet of the invention which shows the extrusion of a portion of the core through a portion of the edge of the tablet which is observed within two hours after a tablet is placed in an aqueous fluid.
Figure 4:
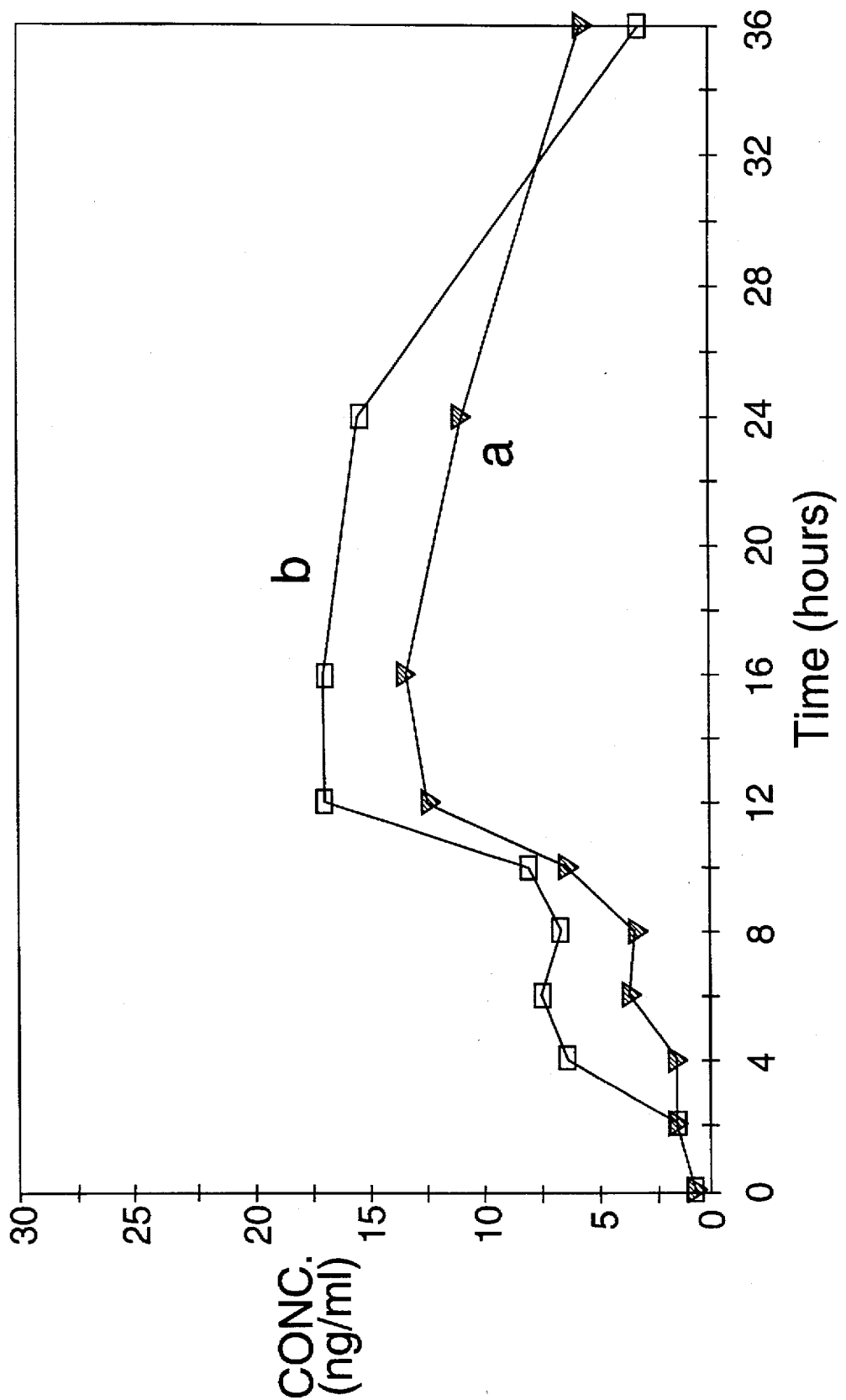
FIG. 4 is a graph which compares the mean plasma concentration of Procardia XL® (b) and a nifedipine tablet (a) prepared according to Example 2 of the present invention in a crossover study involving 6 fasting human volunteers.
Figure 5:
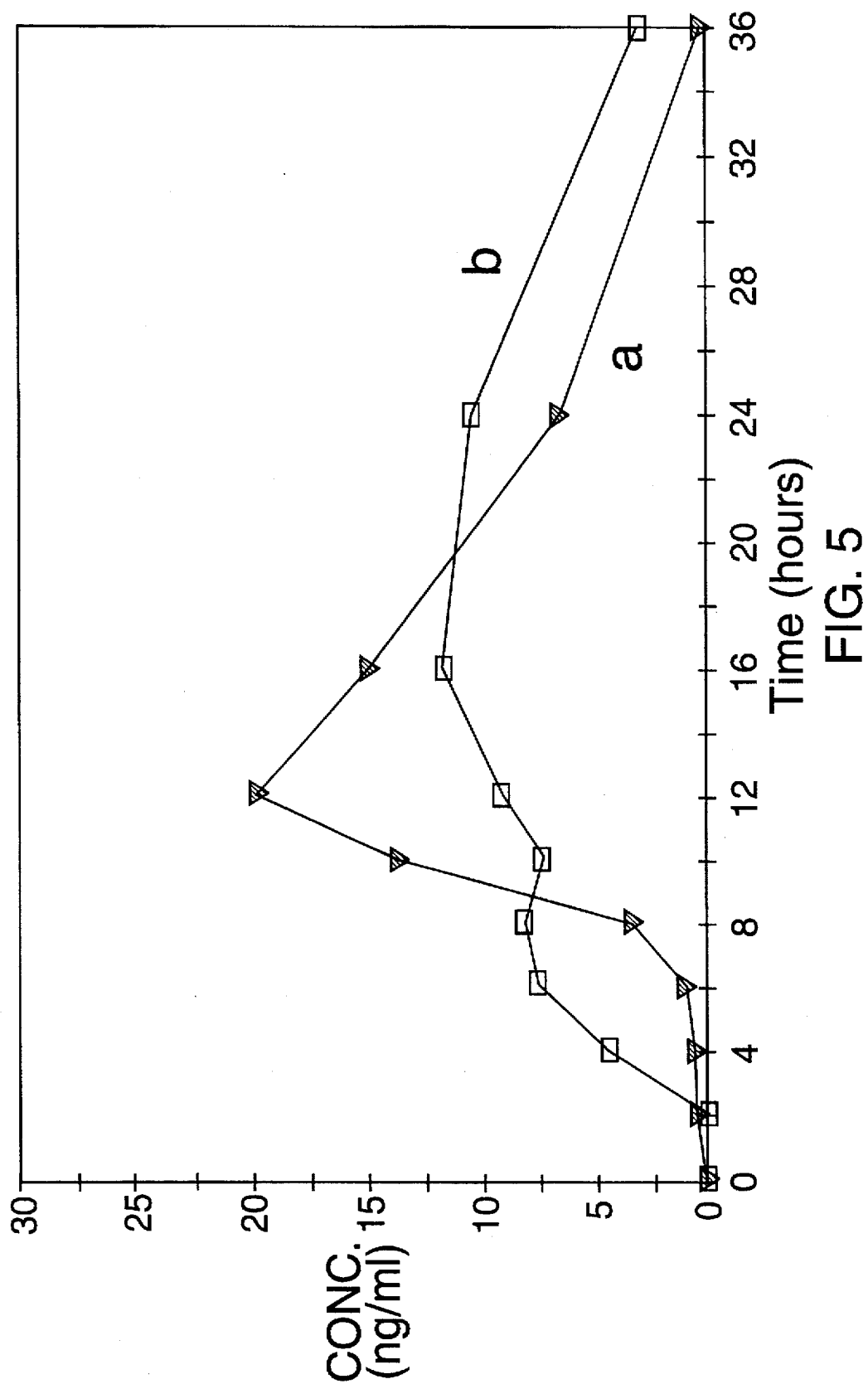
FIG. 5 is a graph which compares the mean plasma concentration of Procardia XL® (b) and a nifedipine tablet (a) prepared according to Example 2 of the present invention in a crossover study involving 6 fed human volunteers.
Figure 6:
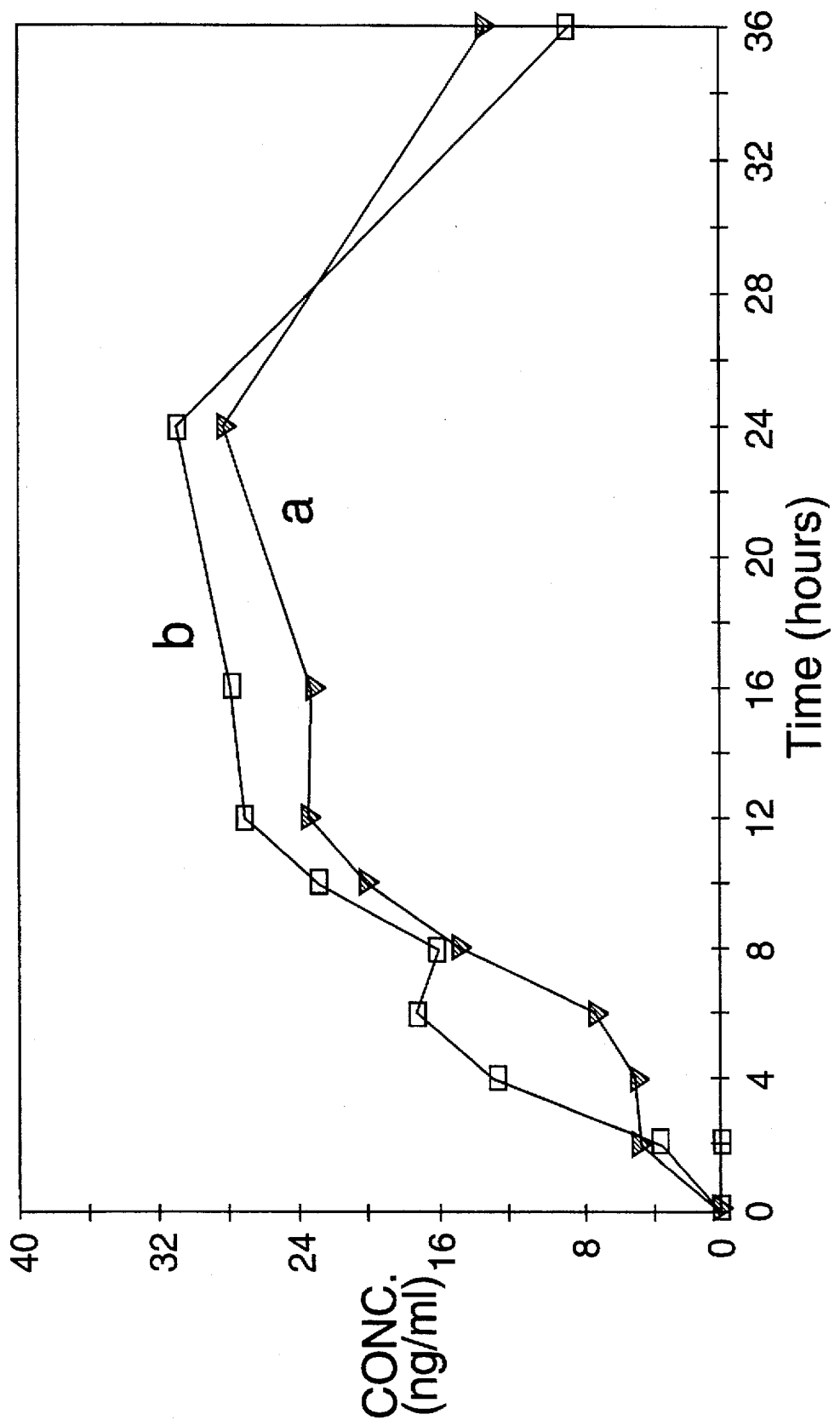
FIG. 6 is a graph which compares the mean plasma concentration of Procardia XL® (b) and a nifedipine tablet (a) prepared according to Example 3 of the present invention in a crossover study involving 6 fasting human volunteers.
Figure 7:
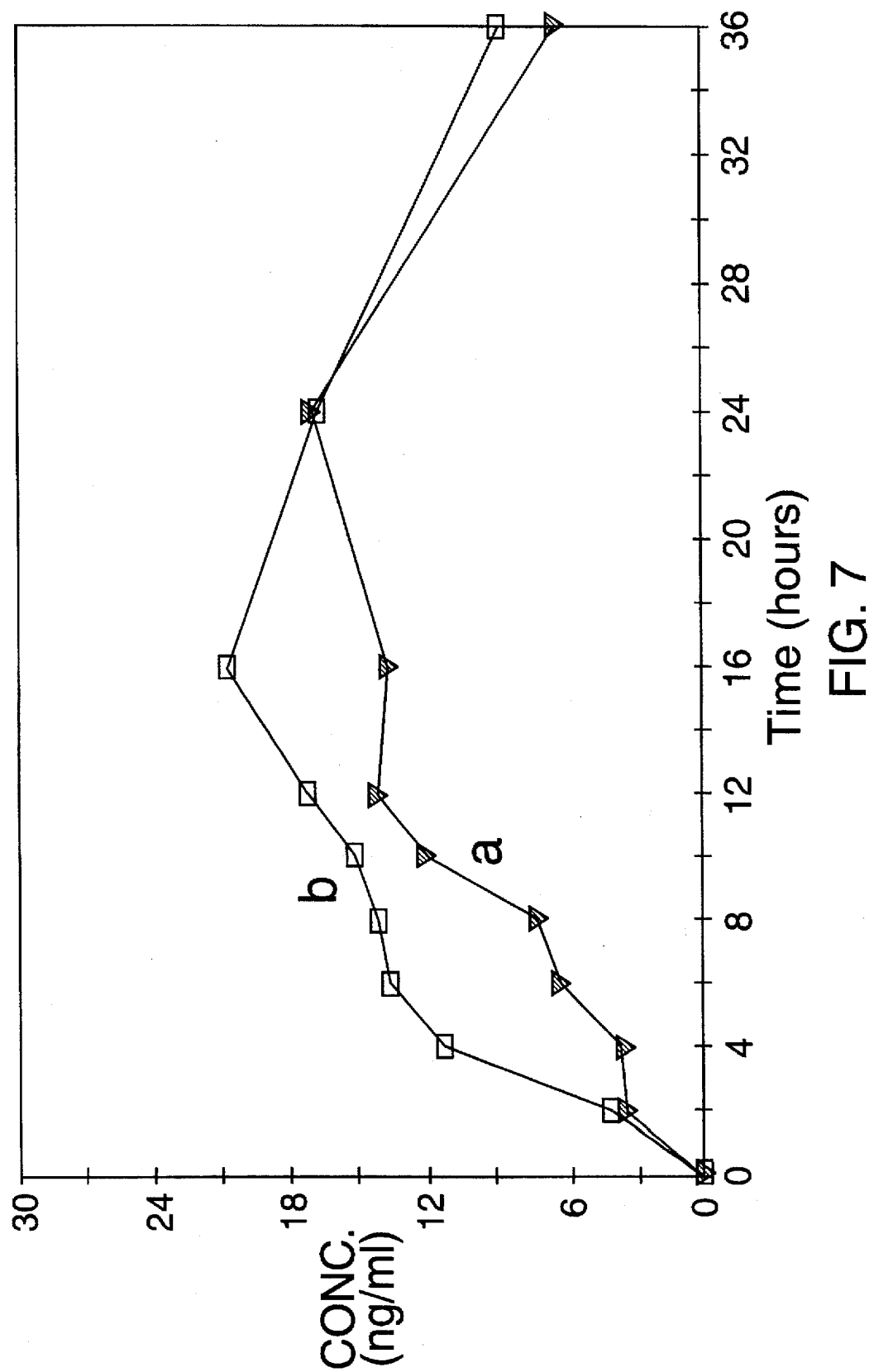
FIG. 7 is a graph which compares the mean plasma concentration of Procardia XL® (b) and a nifedipine tablet (a) prepared according to Example 4 of the present invention in a crossover study involving 6 fasting human volunteers.

The expansion of the core causes a small opening to form at the weakest point in the membrane which is at the edge of the tablet. Once the initial opening is formed at a single point, the osmotic effect of the core components will cause the contents of the core to extrude through the initial opening. The internal pressure which is exerted on the membrane by the swelling and expanding osmotic core is relieved by the passage of the first portion of the core contents through the initial opening and no other opening is observed. This effect is illustrated in FIG. 3 and is unexpected because it could not have been predicted that only a single opening in the membrane would occur rather than a bursting of the membrane. It is believed that the formation of the single opening, without loss of the integrity of the rest of the membrane by uncontrolled expansion of the osmotic core, is responsible for the 24 hour therapeutic blood level which may be achieved by the controlled release tablet of the invention.

FIG. 3 shows a cross-section of a tablet of the invention which illustrates the internal structure of the tablet with core element 10 and membrane 12. The relatively thin membrane at edges 14 and 16 is shown by the cross-section. The extruding portion of the core 18 which is observed after the tablet is placed in an aqueous fluid appears to be resemble an irregularly shaped elastic mass of a portion of the core tablet.

The controlled release tablet of the invention is primarily intended to be used to administer medicaments which are slightly soluble to practically insoluble in water although it may be used with other medicaments having greater solubility. The terms slightly soluble to practically insoluble are used to include those substances which are soluble in from 100 to more than 10,000 parts of water per part of solute.

Examples of categories of medicaments which may be utilized, at therapeutic dose levels, in the controlled release tablets of the invention include anti-hypertensives, calcium channel blockers, analgesics, anti-neoplastic agents, anti-microbials, anti-malarials, non-steroidal anti-inflammatory agents, diuretics, anti-arrythmia agents and the like.

Specific examples of medicaments include nifedipine, nisoldipine, nicardipine, nilvadipine, felodipine, bendroflumethazide, acetazolamide, methazolamide, chlorpropamide, methotrexate, allopurinol, erythromycin, hydrocortisone, triamcinolone, prednisone, prednisolone, norgestrel, norethindone, progesterone, norgesterone, ibuprofen, atenolol, timolol, cimetidine, clonidine, diclofenac and the like.

When a drug such as nifedipine is used in a crystalline form as a starting material to make granules, the crystalline form will be transformed into the amorphous form using a weight ratio of about 2:1 or higher of an agent such as povidone to nifedipine in an organic solvent system such as acetone (5:1 ratio of acetone to nifedipine) and isopropyl alcohol (3:1 ratio of isopropyl alcohol to nifedipine). If, for example, a 5 wt % povidone solution in water is used to form granules, the crystalline nifedipine will remain in the crystalline form in the granules. Blends of crystalline and amorphous forms may be made by physically blending the different forms at different ratios e.g. 80:20 to 20:80 or 50:50.

The water soluble osmotic agent is any non-toxic pharmaceutically acceptable compound which will dissolve sufficiently in water and increase the osmotic pressure inside of the core of the tablet. The osmotic agents are used in effective amounts, which are from 23 to 55% by weight of the total weight of the core, and preferably from 30 to 50% by weight of the total weight of the core tablet. These osmotic agents include sodium chloride, potassium chloride, magnesium sulfate, magnesium chloride, sodium sulfate, lithium sulfate, urea, inositol, sucrose, lactose, glucose, sorbitol, fructose, mannitol, dextrose, magnesium succinate, potassium acid phosphate and the like.

The water soluble binder may be any pharmaceutically acceptable film former which can be utilized to bind the powder mixture together with an adhesive, instead of by compaction, in order to form granules for making compressed tablets. These polymers include polyvinyl pyrrolidone, carboxyvinyl polymer, methylcellulose, hydroxyethylcellulose, hydroxypropylcellulose, hydroxypropylmethylcellulose, dextrin, maltodextrin and the like. These materials are formed into a dispersion or solution in water or other solvent system at a sufficient concentration to have a binding effect on the osmotic agent, the medicament and any excipient. This will generally require a concentration of about of 5 to 15 wt % of the film former.

Generally the binder is used in a sufficient amount so that when it is combined with a suitable solvent, combined with the water soluble osmotic agent and agitated, granules will be formed which may be compressed into a tablet core. Prior to compressing the granules, a water swellable polymer and one or more conventional pharmaceutical excipients such as microcrystalline cellulose, lactose, dextrose and the like are added to the granule forming mixture in an amount which will aid in forming granules which are compressible to form a tablet core. Generally these amounts will range from about 5 to 20 wt % based on the weight of the compressed core.

Suitable pharmaceutically acceptable, water swellable polymers include polyethylene oxide having a molecular weight of 100,000 to 5,000,000; poly(hydroxy alkyl methacrylate) having a molecular weight of from 30,000 to 5,000,000; poly(vinyl) alcohol, having a low acetal residue, which is cross-linked with glyoxal, formaldehyde or glutaraldehyde and having a degree of polymerization of from 200 to 30,000; a mixture of methyl cellulose, cross-linked agar and carboxymethyl cellulose; a water insoluble, water swellable copolymer produced by forming a dispersion of a finely divided copolymer of maleic anhydride with styrene, ethylene, propylene, butylene or isobutylene cross-linked with from 0.001 to 0.5 moles of saturated cross-linking agent of saturated cross-linking agent per mole of maleic anyhydride in the copolymer; Carbopol® acidic carboxy polymers having a molecular weight of 450,000 to 4,000,000; Cyanamer® polyacrylamides; cross-linked water swellable indene-maleic anhydride polymers; Goodrite® polyacrylic acid having a molecular weight of 80,000 to 200,000; starch graft copolymers; Aqua-Keeps® acrylate polymer polysaccharides composed of condensed glucose units such as diester cross-linked polyglucan and the like. Other polymers which form hydrogels are described in U.S. Pat. No. 3,865,108; U.S. Pat. No. 4,002,173 and U.S. Pat. No. 4,207,893 all of which are incorporated by reference. The pharmaceutically acceptable, water swellable polymers may be employed in an effective amount that will control the swelling of the tablet core. These amounts will generally be from about 3 to 12 wt %, preferably from about 5 to 10 wt % based on the weight of the compressed tablet core.

The membrane coating around said core consists essentially of a plasticized water insoluble pharmaceutically acceptable polymer. Suitable water insoluble polymers include cellulose esters, cellulose ethers and cellulose ester-ethers. The celluosic polymers have a degree of substitution greater than 0 up to 3. The degree of substitution is calculated as the average number of original hydroxyl groups on the anhydroglucose unit which makes up the cellulose polymer which are replaced with a substitute group. These materials include cellulose acylate, cellulose ethyl ether, cellulose diacylate, cellulose triacylate, cellulose acetate, cellulose diacetate, cellulose triacetate, mono-, di- and tricellulose alkan, mono-, di- and tricellulose aroyl and the like. Cellulose triacetate is the preferred polymer. Other water insoluble polymers are disclosed in U.S. Pat. No. 4,765,989 which is incorporated by reference. If desired other polymers may be combined with the water insoluble polymer to modify the permeability of the membrane coating around the core. These include hydroxymethyl cellulose, hydroxypropyl cellulose or cellulose per se. Generally, the membrane coating around the core will comprise from about 2 to 10 wt % preferably about 4 to 8 wt % based on the total weight of the core tablet.

The modified water insoluble polymer may contain a plasticizer or a water soluble channeling agent as the modifier. The water soluble channeling agent is a material that dissolves in water to form a porous polymer shell that allows water to be imbibed into the core. This material is used in a sufficient amount that channels will form in the water insoluble polymer. These materials include water soluble organic and inorganic compounds such as sucrose, lactose, dextrose, sodium chloride, sorbic acid, potassium chloride, polyethylene glycol (weight av. molecular weight 380–420), propylene glycol and mixtures thereof.

The water insoluble polymer may be plasticized with a plasticizing amount of a plasticizer. The preferred plasticizer is triacetin but materials such as acetylated monoglyceride, rape oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer or water soluble channeling agent, amounts of from 1% to 40%, and preferably 10 to 30% of the modifier based on the total weight of the water insoluble polymer, water soluble polymer and the modifier may be utilized.

In the preparation of the tablets of the invention, various conventional well known solvents may be used to prepare the granules and apply the external coating to the tablets of the invention. In addition, various diluents, excipients, lubricants, dyes, pigments, dispersants etc. which are disclosed in Remington's Pharmaceutical Sciences, 1985 Edition may be used to optimize the formulations of the invention.

DESCRIPTION OF THE PREFERRED EMBODIMENTS

Example 1

Tablets having the following formula are prepared as follows:

| I Granulation | |
|---|---|
| nifedipine | 12.64 wt % |
| povidone[1], USP | 25.29 wt % |
| sodium chloride, USP powder | 57.47 wt % |
| microcrystalline cellulose, NF | 3.6 wt % |
| polysorbate 80, NF | 1.0 wt % |
| acetone* (Five times the amount of nifedipine) | |
| isopropyl alcohol* (Three times the amount of nifedipine) | |

[1]weight average molecular weight = 55,000; freely soluble in water (1 g in 1–10 ml of water); dynamic viscosity (10% w/v solution at 20° C.) = 5.5–8.5 m Pa s.
*acetone and isopropyl alcohol are evaporated during the granulation process.

(a) The nifedipine is first dispersed in acetone and then the povidone is added with stirring until a uniform mixture is formed. The isopropyl alcohol is then added and mixed until a clear solution is formed. The polysorbate 80 is added and the product is continuously stirred until it is used.

(b) The sodium chloride and microcrystalline cellulose is placed in a fluidized bed dryer to make granules. The solution of the nifedipine, which has been separately prepared in step (a), is sprayed onto the sodium chloride/microcrystalline mixture to make granules. After completion of the granulation step, initiate the drying cycle. Continue the drying until the moisture loss on drying (LOD) is not more than 2.5%.

| II Tabletting | |
|---|---|
| granules (I) | 87.0 wt % |
| microcrystalline cellulose, NF | 5.0 wt % |
| poly(ethyleneoxide)[2], nf | 7.0 wt % |
| magnesium stearate, NF | 1.0 wt % |

[2]Polyox ® WSR-NF; approximate molecular weight = 7,000,000.

(c) A tablet core is made by adding 7.0 wt % of poly (ethyleneoxide), NF; 1.0 wt % of magnesium stearate; 5.0 wt % of microcrystalline cellulose; and 87.0 wt % of the granules from step (b), based on the total weight of all ingredients. Core tablets weighing 300 mg each are made in a tablet press machine with 0.3410" standard concave punches and die.

| III Sustained Release Coating | |
|---|---|
| cellulose acetate | 53.58 wt % |
| hydroxypropyl cellulose, NF (Klucel ® EF)[3] | 26.80 wt % |
| triacetin | 11.32 wt % |
| polyethylene glycol 400 | 8.30% |

[3]Klucel ® EF,NF; viscosity 200–600 cps; (10% soln. H₂O, 25° C.) Mw$_n$ = 80,000; hydroxy/propyl ratio = 3.4–4.4 Particle size; 20 and above mesh = 0 wt % retained; 30 and above mesh size = 2.2 wt % retained; total through 30 mesh 97.8 wt %

(d) A sustained release coating is applied to the tablets prepared in step (c) by coating the tablets with a coating solution of formula (III).

The coating is applied by a fluid bed coater until the tablets exhibit a weight gain of 6%.

Example 2

Tablets having the following formula are prepared as follows:

| (I) Granulation | |
| --- | --- |
| nifedipine, USP | 11.96 wt % |
| sodium chloride, USP powder | 54.35 wt % |
| microcrystalline cellulose, NF | 8.78 wt % |
| povidone[1] USP | 23.91 wt % |
| polysorbate 80, NF | 1.0 wt % |
| purified water* | |
| (sufficient to make a 10 wt % solution | |
| with 5.0 wt % of povidone) | |

[1]weight average molecular weight = 55,000; freely soluble in water (1 g in 1–10 ml of water); dynamic viscosity (10% w/v solution at 20° C.) = 5.5–8.5 m Pa s.
*water is evaporated during the granulation process.

(a) A 5.0 wt % portion based on the total weight of the solid ingredients, is used to form a solution with 10 times the weight of a 5 wt % portion of the povidone to make a 10 wt % solution of povidone in water. The polysorbate 80 is added to the solution and the product is continuously stirred until it is used.

(b) The sodium chloride, microcrystalline cellulose, nifedipine and the balance of the povidone, 18.91 wt % based on the total weight of the ingredients, are placed in a fluid bed dryer. The povidone solution, which was separately prepared, is sprayed onto the mixture of sodium chloride, microcrystalline cellulose, nifedipine and the povidone to make granules. After completion of the granulation process, the drying cycle is initiated and continued until the loss on drying (LOD) is not more than 2.5% at about 60° C. Then, the dried granules are sized to 40 mesh (USS standard screen) in an oscillating granulator.

| II Tabletting | |
| --- | --- |
| granules (from I) | 90.0 wt % |
| poly(ethylene oxide)[2], NF | 9.0 wt % |
| magnesium stearate, NF | 1.0 wt % |

[2]Polyox ® WSR-NF; approximate molecular weight = 7,000,000.

(c) A mixture for making a core tablet is made by adding 9 wt % of poly(ethylene oxide), 1 wt % of magnesium stearate and 90 wt % of the granules, based on the total weight of the three ingredients, prepared previously. Core tablets weighing 307 mg each are made on a tablet press using 0.3410" standard concave punches and die.

| III Sustained Release Coating | |
| --- | --- |
| cellulose acetate | 46.28 wt % |
| hyroxypropyl cellulose, NF (Klucel ® EF) | 23.14 wt % |
| triacetin, USP | 9.76 wt % |
| polyethylene glycol 400 | 20.82 wt % |

(d) The sustained release coating is applied to the tablets that were prepared in step (c) by coating the tablets with the above described coating solution (III). The coating was applied by using a fluid bed coater until the tablets exhibited a weight gain of 6%.

Example 3

Tablets having the following formula are prepared as follows:

| I Granulation | |
| --- | --- |
| nifedipine | 12.65 wt % |
| povidone[1], USP | 30.62 wt % |
| sodium chloride, USP powder | 28.72 wt % |
| microcrystalline cellulose, NF | 9.29 wt % |
| hydroxypropyl methylcellulose (Methocel K-100M)[2] | 17.66 wt % |
| polysorbate 80, NF | 1.06 wt % |
| acetone* | |
| (Five times the amount of nifedipine) | |
| isopropyl alcohol* | |
| (Three times the amount of nifedipine) | |

[1]weight average molecular weight = 55,000; freely soluble in water (1 g in 1–10 ml of water); dynamic viscosity (10% w/v solution at 20° C.) = 5.5–8.5 m Pa s.
*acetone and isopropyl alcohol are evaporated during the granulation process.
[2]hydroxypropyl methylcellulose having a molecular weight of 246,000 $(Mw_w)$.

(a) The nifedipine is first dispersed in acetone and then the povidone is added with stirring until a uniform mixture is formed. The isopropyl alcohol is then added and mixed until a clear solution is formed. The polysorbate 80 is then added and the product is continuously stirred until it is used.

(b) The sodium chloride, hyudroxypropyl methylcellulose and microcrystalline cellulose is placed in a fluidized bed dryer to make granules. The solution of the nifedipine, which has been separately prepared in step (a), is sprayed onto the sodium chloride/hydroxypropyl methyl cellulose/ microcrystalline mixture to make granules. After completion of the granulation step, initiate the drying cycle. Continue the drying until the moisture loss on drying (LOD) is not more than 2.5%.

| II Tabletting | |
| --- | --- |
| granules (I) | 85.0 wt % |
| sodium chloride, USP powder | 5.0 wt % |
| poly(ethyleneoxide)[2], nf | 9.0 wt % |
| magnesium stearate, NF | 1.0 wt % |

[2]Polyox ® WSR-NF; approximate molecular weight = 7,000,000.

(c) A tablet core is made by adding 9.0 wt % of poly(ethyleneoxide), NF; 1.0 wt % of magnesium stearate; 5.0 wt % of sodium chloride; and 85.0 wt % of the granules from step (b), based on the total weight of all ingredients. Core tablets weighing 307 mg each are made in a tablet press machine with 0.3410" standard concave punches and die.

| III Sustained Release coating | |
| --- | --- |
| cellulose acetate | 46.29 wt % |
| hydroxypropyl cellulose (Klucel ® EF) | 23.15 wt % |
| triacetin | 9.76 wt % |
| polyethylene glycol 400 | 20.80 wt % |

(d) A sustained release coating is applied to the tablets prepared in step (c) by coating the tablets with a coating solution of formula (III)

The coating is applied by a fluid bed coater until the tablets exhibit a weight gain of 6%.

Example 4

Tablets having the following formula are prepared as follows:

| I Granulation | |
|---|---|
| nifedipine | 12.65 wt % |
| povidone[1], USP | 30.62 wt % |
| sodium chloride, USP powder | 28.72 wt % |
| microcrystalline cellulose, NF | 9.29 wt % |
| hydroxypropyl methylcellulose (Methocel K-100M) | 17.66 wt % |
| polysorbate 80, NF | 1.06 wt % |
| acetone* (Five times the amount of nifedipine) | |
| isopropyl alcohol* (Three times the amount of nifedipine) | |

[1] weight average molecular weight = 55,000; freely soluble in water (1 g in 1–10 ml of water); dynamic viscosity (10% w/v solution at 20° C.) = 5.5–8.5 m Pa s.
*acetone and isopropyl alcohol are evaporated during the granulation process.

(a) The nifedipine is first dispersed in acetone and then the povidone is added with stirring until a uniform mixture is formed. The isopropyl alcohol is then added and mixed until a clear solution is formed. The polysorbate 80 is added and the product is continuously stirred until it is used.

(b) The sodium chloride, hydroxypropyl methylcellulose and microcrystalline cellulose is placed in a fluidized bed dryer to make granules. The solution of the nifedipine, which has been separately prepared in step (a), is sprayed onto the sodium chloride/hydroxypropyl methyl cellulose/microcrystalline mixture to make granules. After completion of the granulation step, initiate the drying cycle. Continue the drying until the moisture loss on drying (LOD) is not more than 2.5%.

| II Tabletting | |
|---|---|
| granules (I) | 85.0 wt % |
| hydroxypropyl methyl cellulose (Methocel K-100 M) | 5.0 wt % |
| poly(ethyleneoxide)[2], nf | 9.0 wt % |
| magnesium stearate, NF | 1.0 wt % |

[2] Polyox ® WSR-NF; approximate molecular weight = 7,000,000.

(c) A tablet core is made by adding 9.0 wt % of poly(ethyleneoxide), NF; 1.0 wt % of magnesium stearate; 5.0 wt % of sodium chloride; and 85.0 wt % of the granules from step (b), based on the total weight of all ingredients. Core tablets weighing 307 mg each are made in a tablet press machine with 0.3410" standard concave punches and die.

| III Sustained Release coating | |
|---|---|
| cellulose acetate | 46.29 wt % |
| hydroxypropyl cellulose (Klucel ® EF) | 23.15 wt % |
| triacetin | 9.76 wt % |
| polyethylene glycol 400 | 20.80 wt % |

(d) A sustained release coating is applied to the tablets prepared in step (c) by coating the tablets with a coating solution of formula (III)

The coating is applied by a fluid bed coater until the tablets exhibit a weight gain of 6%.

Example 5

Tablets having the following formula are prepared as follows:

| I Granulation | |
|---|---|
| nifedipine | 12.65 wt % |
| povidone[1], USP | 30.62 wt % |
| sodium chloride, USP powder | 28.72 wt % |
| microcrystalline cellulose, NF | 9.29 wt % |
| hydroxypropyl methylcellulose (Methocel K-100 M) | 17.66 wt % |
| polysorbate 80, NF | 1.06 wt % |
| acetone* (Five times the amount of nifedipine) | |
| isopropyl alcohol* (Three times the amount of nifedipine) | |

[1] weight average molecular weight = 55,000; freely soluble in water (1 g in 1–10 ml of water); dynamic viscosity (10% w/v solution at 20° C.) = 5.5–8.5 m Pa s.
*acetone and isopropyl alcohol are evaporated during the granulation process.

(a) The nifedipine is first dispersed in acetone and then the povidone is added with stirring until a uniform mixture is formed. The isopropyl alcohol is then added and mixed until a clear solution is formed. The polysorbate 80 is added and the product is continuously stirred until it is used.

(b) The sodium chloride, hyudroxypropyl methylcellulose and microcrystalline cellulose is placed in a fluidized bed dryer to make granules. The solution of the nifedipine, which has been separately prepared in step (a), is sprayed onto the sodium chloride/hydroxypropyl methyl cellulose/microcrystalline mixture to make granules. After completion of the granulation step, initiate the drying cycle. Continue the drying until the moisture loss on drying (LOD) is not more than 2.5%.

| II Tabletting | |
|---|---|
| granules (I) | 85.0 wt % |
| hydroxypropyl methyl cellulose (Methocel K-100 M) | 5.0 wt % |
| poly(ethyleneoxide)[2], nf | 9.0 wt % |
| magnesium stearate, NF | 1.0 wt % |

[2] Polyox ® WSR-NF; approximate molecular weight = 7,000,000.

(c) A tablet core is made by adding 9.0 wt % of poly(ethyleneoxide), NF; 1.0 wt % of magnesium stearate; 5.0 wt % of sodium chloride; and 85.0 wt % of the granules from step (b), based on the total weight of all ingredients. Core tablets weighing 307 mg each are made in a tablet press machine with 0.3410" standard concave punches and die.

| III Sustained Release coating | |
|---|---|
| cellulose acetate | 46.29 wt % |
| hydroxypropyl cellulose, NF (Klucel ® EF) | 23.15 wt % |
| triacetin | 9.76 wt % |
| sucrose (confectioners NF) | 20.80 wt % |

(d) A sustained release coating is applied to the tablets prepared in step (c) by coating the tablets with a coating solution of formula (III)

The coating is applied by a fluid bed coater until the tablets exhibit a weight gain of 6%.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A controlled release pharmaceutical tablet which comprises:
a) a compressed core which consists essentially of:
   (i) a calcium channel blocker;
   (ii) at least 23% to 55% by weight, based on the total weight of the core, of a water soluble osmotic agent;
   (iii) a water soluble pharmaceutically acceptable polymeric binder;
   (iv) a water-swellable pharmaceutically acceptable polymer; and
(b) a membrane coating around said core tablet which consists essentially of triacetin plasticized cellulose acetate, hydroxypropyl cellulose and polyethylene glycol.

2. A controlled release pharmaceutical tablet which comprises:
a) a compressed core which consists essentially of:
   (i) a calcium channel blocker;
   (ii) at least 23% to 55% by weight, based on the total weight of the core, of a water soluble osmotic agent;
   (iii) a water soluble pharmaceutically acceptable polymeric binder;
   (iv) a water-swellable pharmaceutically acceptable polymer; and
(b) a membrane coating around said core tablet which consists essentially of triacetin plasticized sucrose and hydroxypropyl cellulose.

3. A controlled release pharmaceutical tablet as defined in claim 1 wherein the calcium channel blocker is nifedipine in crystalline form and the water swellable polymer is a poly(ethylene oxide).

4. A controlled release pharmaceutical tablet as defined in claim 1 wherein the calcium channel blocker is nifedipine in amorphous form and the water swellable polymer is a poly(ethylene oxide).

5. A controlled release pharmaceutical tablet as defined in claim 1 wherein the calcium channel blocker is nifedipine as a blend of the crystalline and amorphous forms and the water swellable polymer is a poly(ethylene oxide).

6. A controlled release pharmaceutical tablet which comprises:
a) a compressed core which consists essentially of:
   (i) a calcium channel blocker;
   (ii) at least 23% to 55% by weight, based on the total weight of the core, of a water soluble osmotic agent;
   (iii) a water soluble pharmaceutically acceptable polymeric binder;
   (iv) a water-swellable pharmaceutically acceptable polymer;
   (v) microcrystalline cellulose and polysorbate 80; and
(b) a membrane coating around said core tablet which consists essentially of triacetin plasticized cellulose acetate, hydroxypropyl cellulose and polyethylene glycol.

* * * * *